United States Patent
Lawrenson et al.

(10) Patent No.: US 12,131,662 B2
(45) Date of Patent: Oct. 29, 2024

(54) SYSTEM AND METHOD FOR USE IN ASSISTING A USER TO FOCUS ON PERFORMING A PERSONAL CARE ACTIVITY

(71) Applicant: KONINKLIJKE PHILIPS N.V., Eindhoven (NL)

(72) Inventors: Matthew John Lawrenson, Bussigny-pres-de-Lausanne (CH); Vincentius Paulus Buil, Veldhoven (NL); Lucas Jabobus Franciscus Geurts, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 16/332,953

(22) PCT Filed: Sep. 14, 2017

(86) PCT No.: PCT/EP2017/073182
§ 371 (c)(1),
(2) Date: Mar. 13, 2019

(87) PCT Pub. No.: WO2018/050769
PCT Pub. Date: Mar. 22, 2018

(65) Prior Publication Data
US 2019/0251860 A1 Aug. 15, 2019

(30) Foreign Application Priority Data
Sep. 14, 2016 (EP) .................................. 16188787

(51) Int. Cl.
*G09B 19/00* (2006.01)
*A46B 15/00* (2006.01)
*G16H 20/70* (2018.01)

(52) U.S. Cl.
CPC ...... *G09B 19/0084* (2013.01); *A46B 15/0008* (2013.01); *G16H 20/70* (2018.01); *A46B 15/004* (2013.01); *A46B 15/0044* (2013.01)

(58) Field of Classification Search
CPC . G09B 19/0084; G09B 19/0076; G06F 19/34; G16H 20/70; G16H 40/67;
(Continued)

(56) References Cited

U.S. PATENT DOCUMENTS 8,758,022 B2   6/2014  Kim
2006/0287787 A1* 12/2006 Engstrom .............. G08B 21/06
                                                              701/36
(Continued)

FOREIGN PATENT DOCUMENTS

CN    103859784 A     6/2014
WO    WO2010134049 A1  11/2010
WO    WO2016020803 A1   2/2016

OTHER PUBLICATIONS

Peters C. et al., "Automatic Task Assistance for People with Cognitive Disabilities in Brushing Teeth—a User Study with the TEBRA System", Date: Sep. 29, 2014 (NSR).
(Continued)

*Primary Examiner* — Gregory D. Moseley

(57) ABSTRACT

There is provided a system (100) and method for use in assisting a user to focus on performing a personal care activity. The system (100) comprises a processing unit (102). The processing unit is configured to acquire data associated with the user during the personal care activity, process the acquired data to detect at least one characteristic indicative of a distractive event for the user in performing the personal care activity and initiate one or 5 more actions associated with the detected at least one characteristic
(Continued)

indicative of the distractive event to assist the user in focusing on the personal care activity.

18 Claims, 4 Drawing Sheets

(58) Field of Classification Search
CPC .............. A46B 15/0008; A46B 15/004; A46B 15/0044; A46B 15/0004; A46B 15/0038; G16Z 99/00
See application file for complete search history.

(56) References Cited

U.S. PATENT DOCUMENTS

| | | | |
|---|---|---|---|
| 2008/0109973 A1 | 5/2008 | Farrell | |
| 2008/0256445 A1 | 10/2008 | Olch | |
| 2008/0292151 A1 | 11/2008 | Kurtz | |
| 2009/0307859 A1 | 12/2009 | Mottram | |
| 2013/0180061 A1* | 7/2013 | Simeth | A46B 15/0004 15/22.1 |
| 2013/0234826 A1 | 9/2013 | Kuboi | |
| 2013/0295913 A1* | 11/2013 | Matthews, III | H04M 1/72457 455/420 |
| 2014/0065588 A1* | 3/2014 | Jacobson | A46B 17/08 434/263 |
| 2016/0117937 A1* | 4/2016 | Penders | G06F 16/9535 434/236 |

OTHER PUBLICATIONS

Flagg A. et al., "An Intelligent Toothbrush, Machines for Smart Brushing", ACM Transactions on Accessible Computing, vol. V, No. N, p. A-A:35, Jan. 22, 2011 (NSR).
Oral-B Black 7000 with Bluetooth Electric Rechargeable Toothbrush, Proctor & Gamble 2016, Internet Page.
"Bluetooth Toothbrushes are Bored on Brushing", Jan. 11, 2015, Internet Page http://tech.widgetjoy.com/Bluetoothtoothbrushesareboredonbrushing/.
Maragliano P. et al., "Are you smarter than your smart toothbrush?", Dentistry IQ, p. 1-13, Feb. 22, 2016 http://www.dentistryiq.com/articles/2016/02/areyousmarterthanyoursmarttoothbrush.html.
Kim, Seung Jin, et al."Design and Implementation of a Context-Aware Guidance System to Support Dementia Patients' Activities of Daily Living", IPSJ SIG Technical Report, 2007, pp. 159-166.

\* cited by examiner

SYSTEM AND METHOD FOR USE IN ASSISTING A USER TO FOCUS ON PERFORMING A PERSONAL CARE ACTIVITY

CROSS-REFERENCE TO PRIOR APPLICATIONS

This application is the U.S. National Phase application under 35 U.S.C. § 371 of International Application No. PCT/EP2017/073182, filed on Sep. 14, 2016, which claims the benefit of European Patent Application No. 16188787.2, filed on Sep. 14, 2016. These applications are hereby incorporated by reference herein.

FIELD OF THE INVENTION

The invention relates to aiding a user to perform a personal care activity effectively and, in particular, to a system and method for use in assisting a user to focus on performing the personal care activity.

BACKGROUND OF THE INVENTION

A user performing a personal care activity can often become distracted. This can cause the user to lose focus (or concentration) on the personal care activity that they are performing. This can occur during any personal care activity including a tooth care activity (for example, cleaning, brushing or flossing teeth), a skin care activity (for example, treating or cleansing skin), a grooming activity (for example, removing hair such as cutting hair or shaving hair on any part of the body, or brushing or straightening hair), or any other personal care activity.

Often personal care activities require the user to focus on the personal care activity while it is performed in order to achieve a particular result. For example, brushing the teeth is a necessary action to maintain dental hygiene and users are typically recommended to spend two minutes during a brushing session. The user is required to fully focus on the activity during this brushing session for the best results to be achieved. Current electric toothbrushes often have a timer that indicates when a two minute period has finished. During this two minute period the user is encouraged to focus solely on the action of brushing teeth and timed indications can be given to signal the user to switch to cleaning the next section or quadrant.

Some personal care devices are also provided in systems that are capable of stimulating a user to adhere to a personal care routine or to aid a user to perform a task properly. For example, U.S. Pat. No. 8,758,022 B2 discloses an instructional hygiene method in which an instructional hygiene device (which can include a toothbrush) is configured to provide an instruction to a user during operation, which can include instructing the user regarding a tooth-brushing technique, instructing the user to move a toothbrush head in a circular motion or similar.

However, whilst providing indications of timed periods gives the user feedback as to how long the personal care activity is to last and stimulating a user to adhere to a personal care routine aids the user to perform a task properly, there is nothing to prevent the user from being distracted by other sources during the personal care activity. Thus, there is still a risk that the user will lose focus due to distractions. This can negatively impact the quality and effectiveness of the personal care activity.

Also, there are many forms of distractions that might affect the focus of the user during performance of a personal care activity, which makes it hard for the user to avoid being distracted. For example, the user may walk to a new location, the user may actively watch and/or interact with an object, device, or content that is not associated with the personal care activity, a sound, image, or vibration may be activated on a mobile device, interesting content may be played on a radio or television, the user may be called by another person (for example, from another room), and so on.

Therefore, there is a need for an improved system and method to assist a user to focus on performing a personal care activity.

SUMMARY OF THE INVENTION

As noted above, a limitation with existing systems is that there is a risk the user will be distracted by other sources during a personal care activity, which can cause the user to lose focus and this can have a negative impact on the quality and effectiveness of the personal care activity.

Therefore, according to a first aspect of the invention, there is provided a system for use in assisting a user to focus on performing a personal care activity, the system comprising a processing unit. The processing unit is configured to acquire data associated with the user during the personal care activity, process the acquired data to detect at least one characteristic indicative of a distractive event for the user in performing the personal care activity, and initiate one or more actions associated with the detected at least one characteristic indicative of the distractive event to assist the user in focussing on the personal care activity.

In some embodiments, the system may further comprise a memory unit for storing characteristics indicative of distractive events and associated actions to assist the user in focussing on the personal care activity.

In some embodiments, the processing unit may be configured to process the acquired data by comparing the acquired data to the stored characteristics indicative of distractive events to detect at least one characteristic indicative of a distractive event for the user in performing the personal care activity.

In some embodiments, the detected at least one characteristic indicative of a distractive event may be associated with a plurality of actions to assist the user in focussing on the personal care activity and the processing unit may be configured to select one or more of the plurality of actions associated with the detected at least one characteristic indicative of a distractive event to initiate to assist the user in focussing on the personal care activity.

In some embodiments, the one or more actions may be selected based on any one or more of: a ranking assigned to the plurality of actions, an availability of the plurality of actions at a time for initiating the one or more actions, and a condition of the user.

In some embodiments, the data associated with the user may be acquired from at least one sensor.

In some embodiments, the at least one sensor may comprise any one or more of: a visual sensor, an audio sensor, a motion sensor, a presence sensor, a proximity sensor, and a device status sensor.

In some embodiments, the at least one characteristic indicative of a distractive event may comprise a characteristic indicative of a prospective occurrence of the distractive event for the user in performing the personal care activity.

In some embodiments, the processing unit may be configured to initiate one or more counter-measures associated with the detected at least one characteristic indicative of the distractive event to reduce the likelihood of the distractive event distracting the user.

In some embodiments, the processing unit may be configured to initiate one or more counter-measures by any one or more of: rendering a visual, audio, haptic and/or functional stimulus to one or more devices used in the personal care activity, controlling access to one or more devices responsible for the prospective occurrence of the distractive event, and placing a preventative measure on a source of the prospective occurrence of the distractive event.

In some embodiments, the at least one characteristic indicative of a distractive event may comprise a characteristic indicative of a distractive event occurring for the user in performing the personal care activity.

In some embodiments, the processing unit may be configured to initiate one or more notifications associated with the detected at least one characteristic indicative of the distractive event to prompt the user to focus on the personal care activity.

In some embodiments, the processing unit may be configured to initiate one or more notifications by rendering any one or more of: a visual notification to the user, an audio notification to the user, a haptic notification to the user, and a functional notification to one or more devices used in the personal care activity.

According to a second aspect of the invention, there is provided a method performed by a processing unit for use in assisting a user to focus on performing a personal care activity. The method comprises acquiring data associated with the user during the personal care activity, processing the acquired data to detect at least one characteristic indicative of a distractive event for the user in performing the personal care activity, and initiating one or more actions associated with the detected at least one characteristic indicative of the distractive event to assist the user in focussing on the personal care activity.

According to a third aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to the aspects and embodiments described above, the limitations of existing techniques are addressed. For example, the effect of distractive events is avoided or reduced since the one or more actions that are initiated are specifically associated with the distractive events. This is true irrespective of whether those distractive events are already occurring or have the potential to occur. It is thus possible to identify and address current distractions and/or potential future distractions that may otherwise reduce the quality achieved in a personal care activity. In this way, the focus of the user is aided.

There is thus provided an improved system and method for use in assisting a user to focus on performing a personal care activity, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

As noted above, the invention provides an improved system and method for use in assisting a user to focus on performing a personal care activity, which overcomes the existing problems.

Figure 1:
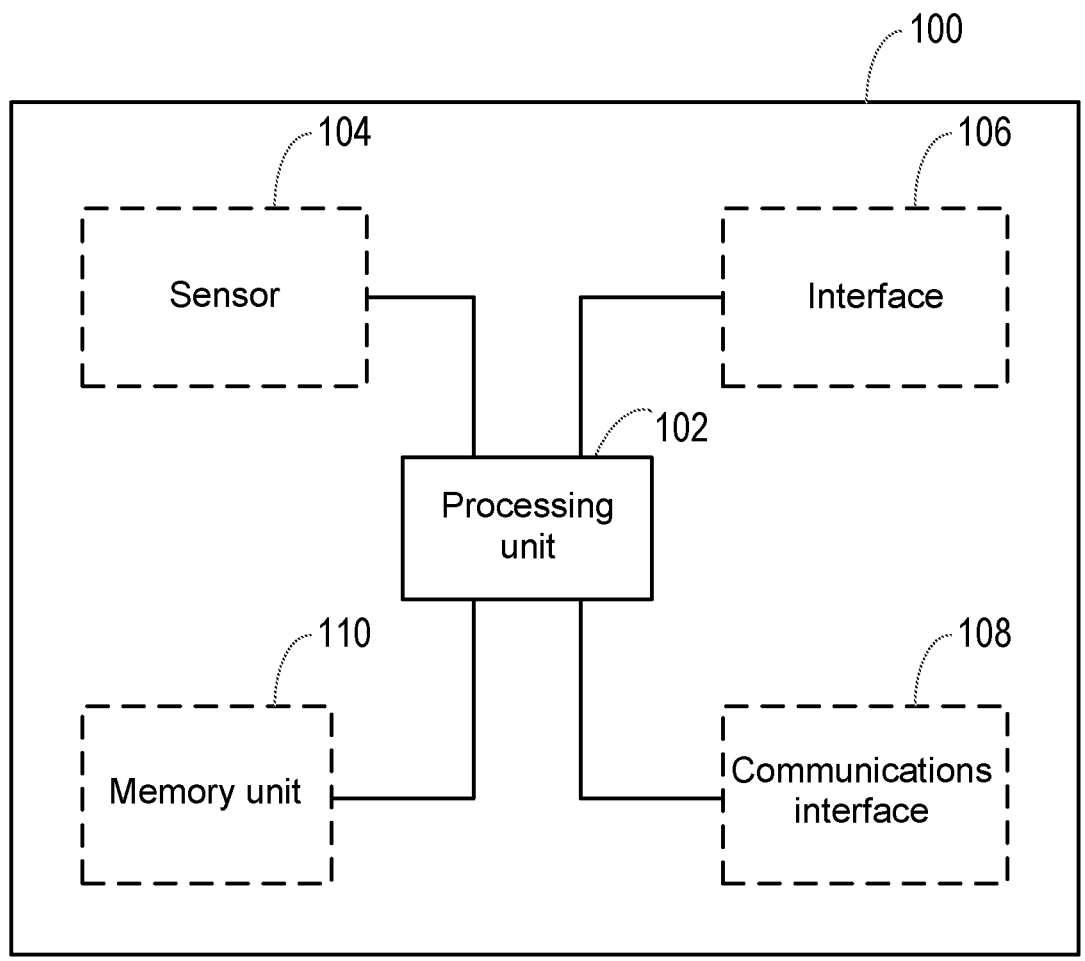
FIG. 1 is a block diagram of a system for use in assisting a user to focus on performing a personal care activity according to an embodiment.

FIG. 1 shows a block diagram of a system 100 according to an embodiment of the invention that can be used for assisting a user to focus on performing a personal care activity. The personal care activity may comprise a tooth care activity (for example, cleaning, brushing or flossing teeth), a skin care activity (for example, treating or cleansing skin), a grooming activity (for example, removing hair such as cutting hair or shaving hair on any part of the body, or brushing or straighten hair), or any other personal care activity.

In some embodiments, a personal care device used in the personal care activity may comprise the system 100. The personal care device may comprise a tooth care device (such as a cleaning device, a toothbrush or a flossing device), a skin care device (such as a treatment or cleansing device), a grooming device (such as a hair removal device, e.g. a hair cutting device, shaver or epilator, a hair brushing device, or hair straighteners), or any other personal care device. Alternatively, in other embodiments, the system 100 may be separate to the personal care device used in the personal care activity.

The system 100 comprises a processing unit 102 that controls the operation of the system 100 and that can implement the method described herein. The processing unit 102 can comprise one or more processors, processing units, multi-core processors or modules that are configured or programmed to control the system 100 in the manner described herein. In particular implementations, the processing unit 102 can comprise a plurality of software and/or hardware modules that are each configured to perform, or are for performing, individual or multiple steps of the method according to embodiments of the invention.

Briefly, the processing unit 102 is configured to acquire data associated with the user during the personal care activity. The data associated with the user can be acquired from at least one sensor 104. The data associated with the user may comprise visual data, audio data, activity or motion data, presence (or absence) data, proximity data, device status data, or any other data, or combination of data associated with the user.

In some embodiments, the processing unit 102 is configured to control one or more sensors 104 to acquire the data. In the illustrated embodiment of FIG. 1, the system 100 comprises one or more sensors 104. However, it will be understood that one or more sensors may alternatively or additionally be external to (i.e. separate to or remote from) the system 100. In some embodiments, the personal care device that is used to perform the personal care activity may comprise one or more sensors. Alternatively or in addition, a device that is not used in the personal care activity may comprise one or more sensors. In some embodiments, the device that is not used in the personal care activity may be a device that is a source (or a potential source) of distraction. Alternatively or in addition, one or more sensors may be provided in the environment of the user.

In some embodiments, one or more sensors 104 may be configured to identify time periods within which the user is distracted or is likely to be distracted. In other words, one or more sensors 104 may be configured to pre-process acquired data to identify sections of data likely to be relevant. In these embodiments, the processing unit 102 may acquire from the one or more sensors 104 data associated with the identified time periods (i.e. the relevant data). For example, the identified time period may be a time period in which the one or more sensors 104 detect a signal indicating the presence of an event or situation that may be relevant to the processing (such as a motion sensor detecting a walking pattern and/or an unusual head tilt of the user, a presence detector detecting the absence of the user, an acoustic sensor detecting speech from the user, or similar). In this way, rather than the processing unit 102 acquiring all of the data on the user from the one or more sensors 104, the processing unit 102 may acquire only data that is relevant, or at least potentially relevant, for processing.

A sensor may be any type of sensor that can acquire data on the user. For example, a sensor can be a visual sensor, an audio sensor, an activity, inertial, or motion sensor, a presence sensor, a proximity sensor, a device status sensor, or any other sensor, or any combination of sensors suitable to acquire data on the user.

A visual sensor may be any sensor suitable to acquire visual data on the user. For example, a visual sensor may be an image sensor (such as a charge-coupled device CCD image sensor, a complementary metal-oxide-semiconductor CMOS image sensor), a camera, a video, an infra-red sensor, or any other visual sensor, or any combination of visual sensors. An audio sensor may be any sensor suitable to acquire audio data on the user. For example, an audio sensor may be a microphone, or any other audio sensor, or any combination of audio sensors. An activity or motion sensor may be any sensor suitable to acquire activity, inertial, or motion data on the user. For example, an activity, inertial, or motion sensor may be an accelerometer, a gyroscope, a magnetometer, a visual sensor, a pressure sensor, or any other inertial, activity or motion sensor, or any combination of inertial, activity or motion sensors. A presence sensor may be any sensor suitable to acquire presence (or absence) data on the user. For example, a presence sensor may be a contact sensor, touch sensor, or pressure sensor (such as in a floor mat), a (body) temperature sensor, a camera (which may comprise a facial recognition component). A proximity sensor may be any sensor suitable to acquire proximity data on the user. For example, a proximity sensor may be an infrared proximity sensor, a camera, an acoustic proximity sensor (such as an ultrasound proximity sensor), or any other proximity sensor, or any combination of proximity sensors. A device status sensor may be any sensor suitable to acquire data on a device associated with the user. For example, a device status sensor may be a sensor that can detect a device being turned on or off by the user, a sensor that can detect user interaction with a device, a sensor that can detect an internet browser being opened (such as from a mobile device or computer), or any other device status sensor, or any combination of device status sensors.

Although examples have been provided for the type of sensor that can acquire data on the user and for the arrangement of sensors, it will be understood that any sensor suitable to acquire data on the user, or any combination of sensors suitable to acquire data on the user, and any arrangement of sensors can be used. In some embodiments, multiple types of sensors can be used.

The processing unit 102 is also configured to process the acquired data to detect at least one characteristic indicative of a distractive event for the user in performing the personal care activity. In some embodiments, the processing unit 102 is configured to process the acquired data by comparing the acquired data to the stored characteristics indicative of distractive events to detect at least one characteristic indicative of a distractive event for the user in performing the personal care activity.

The processing unit 102 is also configured to initiate one or more actions associated with the detected at least one characteristic indicative of the distractive event to assist the user in focussing on the personal care activity. In some embodiments, the processing unit 102 may be configured to initiate one or more counter-measures associated with the detected at least one characteristic indicative of the distractive event to assist the user in focussing on the personal care activity. For example, the processing unit 102 may be configured to initiate one or more counter-measures by rendering a visual, audio, haptic and/or functional stimulus to one or more devices used in the personal care activity, by controlling access to one or more devices responsible for the prospective occurrence of the distractive event, by placing a preventative measure on a source of the prospective occurrence of the distractive event, or by any other counter-measure, or any combination of counter measures.

Alternatively or in addition to a counter-measure, the processing unit 102 may be configured (or further configured) to initiate one or more notifications associated with the detected at least one characteristic indicative of the distractive event to assist the user in focussing on the personal care activity. For example, the processing unit 102 may be configured to initiate one or more notifications by rendering a visual notification to the user, an audio notification to the user, a haptic notification to the user, a functional notification to one or more devices used in the personal care activity, or any other notification, or any combination of notifications.

In some embodiments, the detected at least one characteristic indicative of a distractive event may be associated with a plurality of actions to assist the user in focussing on the personal care activity. In these embodiments, the processing unit 102 may be configured to select one or more of the plurality of actions associated with the detected at least one characteristic indicative of a distractive event to initiate to assist the user in focussing on the personal care activity.

According to some embodiments, the system 100 may also comprise at least one user interface 106. Alternatively or in addition, a user interface 106 may be external to (i.e. separate to or remote from) the system 100. For example, the user interface 106 may be part of another device. In some embodiments, one or more user interfaces may be provided in a personal care device that is used in the personal care activity, one or more user interfaces may be provided in a smart mirror used in the personal care activity, one or more user interfaces may be provided in a device not used in the personal care activity such as a device that is a potential source of distraction for the user (for example, a device in the locality of the user), and/or the user interface may include a light in the environment of the user.

A user interface 106 may be for use in providing the user of the system 100 with information resulting from the method according to the invention. The processing unit 102 may be configured to control one or more user interfaces 106 to provide information resulting from the method according to the invention. For example, in some embodiments, the processing unit 102 may be configured to control one or more user interfaces 106 to render or output one or more initiated actions (such as counter-measures and/or notifications) indicative of the distractive event to assist the user in focussing on the personal care activity, or any other information, data or signals resulting from the methods described herein. Alternatively or in addition, a user interface 106 may be configured to receive a user input. In other words, a user interface 106 may allow the user of the system 100 to manually enter data, instructions, or information.

Thus, a user interface 106 may be or may comprise any component that enables rendering or output of information, data or signals to the user of the system 100. Alternatively or in addition, a user interface 106 may be or may comprise any component that enables the user of the system 100 to provide a user input, interact with and/or control the system 100. For example, the user interface 106 may comprise one or more switches, one or more buttons, a keypad, a keyboard, a touch screen or an application (for example, on a tablet or smartphone), a display screen or other visual indicator, one or more speakers (for example, a loud speaker), one or more microphones, any other voice dialogue components, one or more lights, a component for providing tactile or haptic feedback (for example, a vibration function, a temperature change function), or any other user interface components, or combination of user interface components.

In embodiments where the processing unit 102 is configured to initiate one or more counter-measures associated with the detected at least one characteristic indicative of the distractive event, the processing unit 102 may be configured to control at least one user interface 106 (which may be internal to the system 100 or external to the system 100, as described earlier) to render or provide the one or more counter-measures. Thus, the at least one user interface 106 is controllable (or operable) to render or provide the one or more counter-measures to the user.

In some counter-measure embodiments, at least one user interface 106 of one or more personal care devices used in the personal care activity (for example, a toothbrush, a smart mirror, or any device used in the personal care activity) may be controllable to provide a visual, an audio, a haptic and/or a functional stimulus. In this way, the attention of the user can be drawn to the personal care activity. In one example, at least one user interface 106 of one or more personal care devices used in the personal care activity may be controllable to provide a vibration, a change in temperature, or any other stimulus to the user performing the personal care activity with the personal care device.

Alternatively or in addition, in some counter-measure embodiments, at least one user interface 106 may be controllable to place a preventative measure on a source of a prospective occurrence of a distractive event. In one example, at least one user interface 106 of one or more devices in the environment of the user (other than the personal care device) may be controllable to at least temporarily block any notifications from that device, which may be a potential source of distraction for the user. In another example, at least one user interface 106 of one or more devices on which the user begins a secondary activity (i.e. an activity in addition to the personal care activity) may be controllable to provide a message to the user to persuade the user to stop the secondary activity.

Alternatively or in addition, in some counter-measure embodiments, at least one user interface 106 of one or more devices responsible for a prospective occurrence of a distractive event may be controllable to control access to those one or more devices. In one example, at least one user interface 106 of one or more devices responsible for a prospective occurrence of a distractive event may be controllable to temporarily hide information that may be a potential source of distraction for the user (such as news, traffic, weather, or other information on a smart mirror, smart phone, television, or similar). In another example, at least one user interface 106 of one or more devices responsible for a prospective occurrence of a distractive event may be controllable to adapt accessibility to functions on the one or more devices (such as a smart phone, smart mirror, television, or similar) that are a potential source of distraction for the user.

In embodiments where the processing unit 102 is configured to initiate one or more notifications associated with the detected at least one characteristic indicative of the distractive event to assist the user in focussing on the personal care activity, the processing unit 102 may be configured to control at least one user interface 106 (which may be internal to the system 100 or external to the system 100, as described earlier) to render or provide the one or more notifications. Thus, the at least one user interface 106 is controllable (or operable) to render or provide the one or more notifications to the user. In some notification embodiments, at least one user interface 106 may be controllable to provide a visual notification to the user, an audio notification to the user, a haptic notification to the user, a functional notification to one or more devices used in the personal care activity, or any other notification, or any combination of notifications.

In one example, at least one user interface 106 of a haptic device (which may be the device used in the personal care activity such as a toothbrush, or may be a wearable device, a mobile device, or similar) may be controllable to provide at least one haptic notification, which can be in the form of a vibration notification, a change in temperature, or any other form of haptic notification. In another example, at least one user interface 106 of an audio device (such as a speaker in a toothbrush, a wearable device, a mobile device, a device in the environment of the user, or similar) may be controllable to provide at least one sound to the user (for example, an instruction to stop a distractive event or to focus on the personal care activity). In another example, at least one user interface 106 of a visual device may be controllable to provide at least one visual notification to the user (for example, providing a light on the personal care device such as on a handle or brush head of a toothbrush, or a visual notification via a smart mirror, a wearable device, a mobile device, lighting in the environment, or similar). In another example, at least one user interface 106 of a personal care device used in the personal care activity be controllable to provide a functional notification (such as varying the speed of a brushing motor on an electric toothbrush, varying a motion pattern of the personal care device, or any other functional notification).

In some embodiments, the system 100 may also comprise a communications interface (or circuitry) 108 for enabling the system 100 to communicate with (or connect to) any components, interfaces, units, sensors and devices that are internal or external to the system 100. The communications interface 108 may communicate with any components, interfaces units, sensors and devices wirelessly or via a wired connection. For example, in the embodiments where one or more user interfaces 106 are external to the system 100, the communications interface 108 may communicate with any external user interfaces wirelessly or via a wired connection. Similarly, in the embodiments where the one or more sensors 104 are external to the system 100, the communications interface 108 may communicate with the external sensors wirelessly or via a wired connection.

In some embodiments, the system 100 may also comprise a memory unit 110 configured to store program code that can be executed by the processing unit 102 to perform the method described herein. The memory unit 110 can also be used to store information, data, signals and measurements made or acquired by the processing unit 102 of the system 100 or by components, interfaces, units, sensors and devices that are external to the system 100. For example, the memory unit 110 may be configured to store characteristics indicative of distractive events and associated actions (such as counter-measures and/or notifications) to assist the user in focussing on the personal care activity, and/or any other data made or acquired by the processing unit 102.

The stored characteristics indicative of distractive events may be pre-defined characteristics and/or characteristics that are accumulated from acquired data over time and processed to correlate those characteristics with situations in which the user actually becomes distracted (i.e. the characteristics may be learnt over time). In some embodiments, the processing unit 102 of the system 100 may be configured to monitor distractive activities and the corresponding impact (or effect) that the distractive activities have on a personal care activity to determine which distractive activities have the greatest impact (or effect) on the user. The processing unit 102 may be configured to control the memory unit 110 to store this data. In these embodiments, the user may be able to select or set one or more actions for the processing unit 102 to initiate based on the data. For example, it may be determined through data analysis that head tilting has a greater impact on the personal care activity than walking and thus the user may decide to select one or more actions to initiate upon detection of head tilting and irregular walking patterns. In some embodiments, one or more thresholds associated with a level of a distractive event may be stored in the memory unit 110 and the processing unit 102 may be configured to initiate one or more actions when a level of a distractive event is determined to be above the associated threshold. For example, a threshold may be a distance and/or time period for which a user is allowed to walk during a personal care activity before the one or more actions are initiated. The processing unit 102 may also be configured to control the memory unit 110 to store the acquired data at least temporarily or at least relevant acquired data that can be used in the detection other characteristics in the future.

It will be appreciated that FIG. 1 only shows the components required to illustrate this aspect of the invention, and in a practical implementation the system 100 may comprise additional components to those shown. For example, the system 100 may comprise a battery or other power supply for powering the system 100 or means for connecting the system 100 to a mains power supply.

Figure 2:
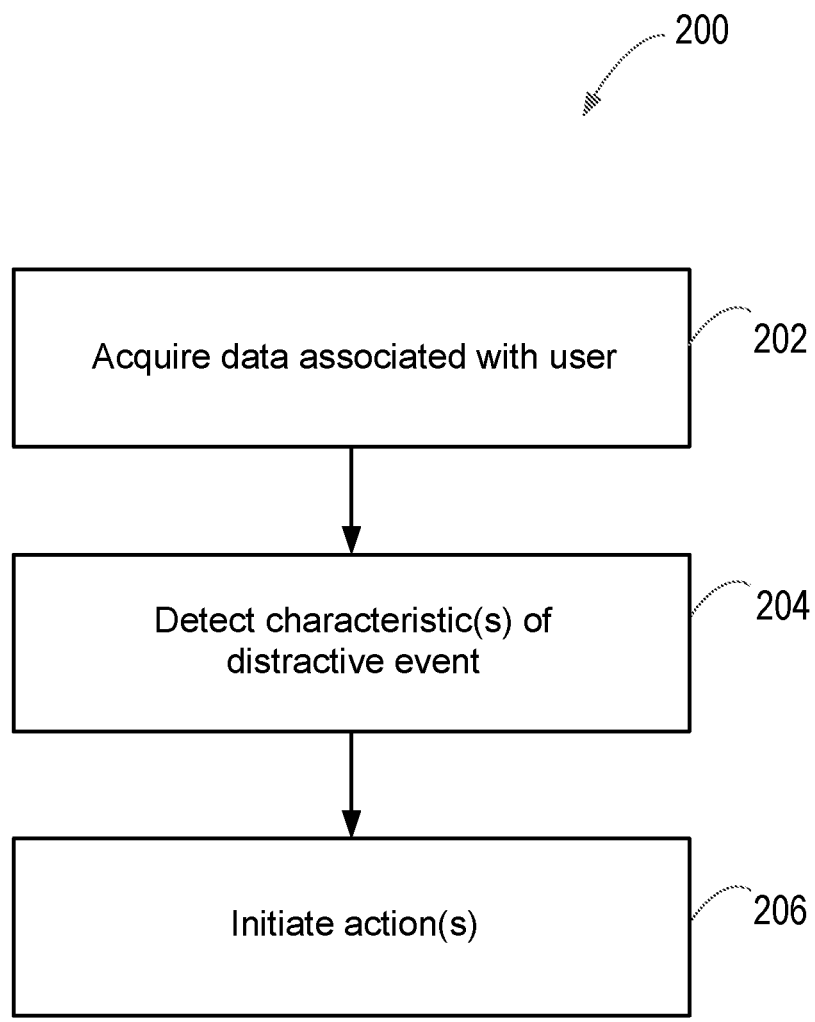
FIG. 2 is a flow chart illustrating a method for use in assisting a user to focus on performing a personal care activity according to an embodiment.

FIG. 2 illustrates a method 200 for use in assisting a user to focus on performing a personal care activity according to an embodiment. The illustrated method 200 can generally be performed by or under the control of the processing unit 102 of the system 100.

With reference to FIG. 2, at block 202, data associated with the user is acquired during the personal care activity. As described earlier, the data associated with the user can be acquired from at least one sensor. For example, the data associated with the user may comprise visual data, audio data, activity or motion data, presence (or absence) data, proximity data, device status data, or any other data, or combination of data associated with the user.

At block 204, the acquired data is processed to detect at least one characteristic indicative of a distractive event for the user in performing the personal care activity. A characteristic indicative of a distractive event is a condition considered to describe a circumstance in which the user is, or is likely to be, distracted. In other words, a characteristic indicative of a distractive event is a signature of a circumstance in which the user is, or is likely to be, distracted. In the case of a plurality of characteristics indicative of a distractive event, the plurality of characteristics are a set of conditions considered to describe (i.e. a set of signatures of) a circumstance in which the user is, or is likely to be, distracted.

In some embodiments, the acquired data may be processed by comparing the acquired data to stored characteristics indicative of distractive events to detect at least one characteristic indicative of a distractive event for the user in performing the personal care activity. For example, as mentioned earlier, the memory unit 110 of the system 100 or an external memory unit may store characteristics indicative of distractive events and associated actions (such as counter-measures and/or notifications) to assist the user in focussing on the personal care activity. Thus, the acquired data may be compared to characteristics indicative of distractive events that are stored in the memory 110 of the system to detect at least one characteristic indicative of a distractive event for the user in performing the personal care activity. Alternatively or in addition, the acquired data may be compared to characteristics indicative of distractive events that are stored in a memory that is external to (or remote from) the system to detect at least one characteristic indicative of a distractive event for the user in performing the personal care activity. In some embodiments, the distractive events and associated actions may be stored in the form of a lookup table (LUT).

In some embodiments, the at least one characteristic indicative of a distractive event may be a single characteristic. For example, the single characteristic may be a location, an indication that proximity to a location has been lost (such as the user moving away from a location associated with the personal care activity), an indication that the user is communication with another person, or any other characteristic. In some embodiments, a location associated with the personal care activity may be determined based on the location of an object associated with the personal care activity (for example, the location of a charging unit for a personal care device used in the personal care activity or a usual location for the personal care activity such as the bathroom for a tooth care activity).

In other embodiments, the at least one characteristic indicative of a distractive event may be a set of characteristics (which may be a set of different characteristics and/or a pattern in a characteristic). For example, the set of characteristics may be a pattern of unusual motion of a personal care device (such as the user walking while performing the personal care activity or at least a pattern not associated with a focussed performance of the personal care activity), a pattern of unusual head motions (such as head rotations, head tilts, or similar), actions of the user indicative of the user performing a secondary activity that is not related to the personal care activity (for example, actions of the user picking up or using a secondary device), or any other set of characteristics. In any embodiments in which more than one characteristic indicative of a distractive event is detected, the characteristics may be indicative of the same distractive event or a different distractive event.

In some embodiments, the at least one characteristic indicative of a distractive event comprises a characteristic indicative of a prospective occurrence of the distractive event for the user in performing the personal care activity (which will be described in more detail later with reference to FIG. 3). In other embodiments, the at least one characteristic indicative of a distractive event comprises a characteristic indicative of a distractive event occurring for the user in performing the personal care activity (which will be described in more detail later with reference to FIG. 4).

As mentioned earlier, each stored characteristic indicative of distractive events is stored with an associated action (such as a counter-measure and/or a notification) to assist the user in focussing on the personal care activity. In some embodiments, each action may be stored with an associated device on which to initiate the action. In some embodiments, each action may be stored with an associated description of the instructions required to carry out the action (which may, for example, be in the form of executable code).

At block 206, one or more actions associated with the detected at least one characteristic indicative of the distractive event are initiated to assist the user in focussing on the personal care activity.

In some embodiments, this may comprise initiating one or more counter-measures associated with the detected at least one characteristic indicative of the distractive event to assist the user in focussing on the personal care activity. For example, as mentioned earlier, one or more counter-measures may comprise rendering a visual, audio, haptic and/or functional stimulus to one or more devices used in the personal care activity, controlling access to one or more devices responsible for a prospective occurrence of the distractive event, placing a preventative measure on a source of a prospective occurrence of the distractive event, or any other counter-measure, or any combination of counter-measures.

Alternatively or in addition to a counter-measure, one or more notifications associated with the detected at least one characteristic indicative of the distractive event may be initiated to assist the user in focussing on the personal care activity. For example, as mentioned earlier, one or more notifications may comprise rendering a visual notification to the user, an audio notification to the user, a haptic notification to the user, a functional notification to one or more devices used in the personal care activity, or any other notification, or any combination of notifications. The notification may act as a warning to the user of a distractive event to encourage the user to remain focussed on the personal care activity (i.e. to ignore the distractive event).

In some embodiments, the detected at least one characteristic indicative of a distractive event may be associated with a plurality of actions to assist the user in focussing on the personal care activity. In these embodiments, one or more of the plurality of actions associated with the detected at least one characteristic indicative of a distractive event may be selected to initiate to assist the user in focussing on the personal care activity. The one or more actions may be selected based on one or more predefined selection criteria. For example, the one or more actions may be selected based on any one or more of a ranking assigned to the plurality of actions (e.g. the actions may be ranked in order of preference for a characteristic), an availability of the plurality of actions at a time for initiating the one or more actions (e.g. an availability of one or more device that can be controlled to provide the one or more actions), and a condition of the user (e.g. the direction the user is facing). Although examples have been provided for the selection criteria that may be used to select one or more actions, it will be understood that other selection criteria, and any combination of selection criteria may be used.

Once one or more actions associated with the detected at least one characteristic indicative of the distractive event have been selected, the one or more actions are initiated and one or more devices are controlled to provide the one or more actions to assist the user in focussing on the personal care activity. In embodiments where the controlled device is external to the system 100, the processing unit 102 can connect to the device via the communications interface 108 to control the device to execute the one or more actions.

Figure 3:
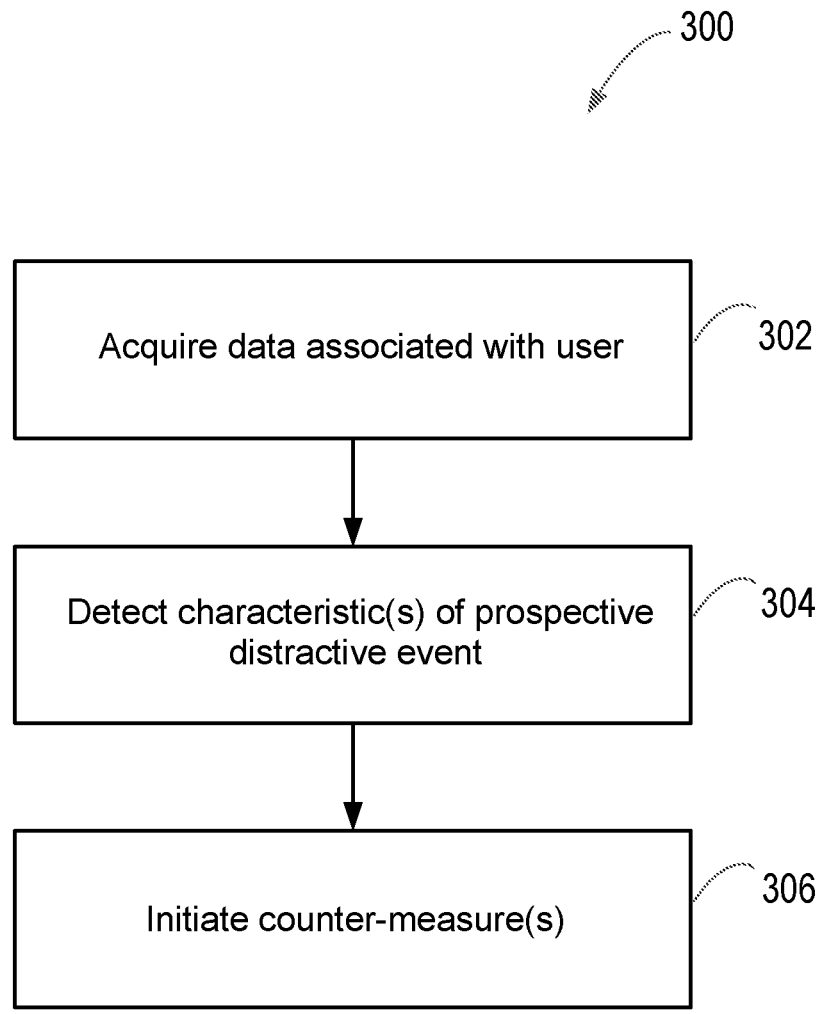
FIG. 3 is a flow chart illustrating a method for use in assisting a user to focus on performing a personal care activity according to one example embodiment.

FIG. 3 illustrates a method 300 for use in assisting a user to focus on performing a personal care activity according to an example embodiment. The illustrated method 300 can generally be performed by or under the control of the processing unit 102 of the system 100. In this example embodiment, it is possible to detect circumstances that can lead to a loss of focus and apply a counter-measure before the user has been affected that circumstance.

With reference to FIG. 3, at block 302, data associated with the user is acquired during the personal care activity. In other words, the method described above with respect to block 202 of FIG. 2 is performed and thus the corresponding description will be understood to apply but will not be repeated here. In this embodiment, the data associated with the user during the personal care activity may be acquired from one or more sensors 106, which can comprise sensors in the environment of the user, in devices other than those used in the personal care activity, and/or any other sensors suitable to acquire data that can be used to identify circumstances that may distract the user in the future.

At block 304, the acquired data is processed to detect at least one characteristic indicative of a prospective occurrence of the distractive event for the user in performing the personal care activity. For example, as described earlier with reference to block 204 of FIG. 2, the acquired data may be processed by comparing the acquired data to stored characteristics indicative of distractive events (i.e. pre-defined signatures of distractive events and/or signatures accumulated over time) stored in a memory unit (such as the memory unit 110 of the system 100 or an external memory unit) to detect at least one characteristic indicative of a distractive event for the user in performing the personal care activity. The processing of the acquired data may be performed in the same manner described for block 204 of FIG. 2 and thus will not be repeated here but will be understood to apply. For example, the characteristics indicative of distractive events may be stored in the memory unit in the form of a look-up table (LUT). As an example, the distractive event may include the user walking around when performing the personal care activity. For example, a sensor in the personal care device may detect the movement of the user and movement patterns of the user can be monitored to detect a situation where the user is walking around.

At block 306, one or more counter-measures associated with the detected at least one characteristic indicative of the distractive event are initiated to reduce the likelihood of the distractive event distracting the user. Specifically, the counter-measure can reduce the likelihood of future distractions. In other words, when at least one characteristic indicative of a distractive event is detected, one or more counter-measures are initiated.

In one example, the initiation of one or more countermeasures may comprise rendering a visual, an audio, a haptic and/or a functional stimulus to one or more devices used in the personal care activity. For example, the stimulus may be specific to keeping the user looking in a certain direction (such as in the case of visual or audio stimulus), or to focussing the user on the personal care device used to perform the personal care activity (such as in the case of audio or haptic stimulus).

In another example, the initiation of one or more countermeasures may comprise controlling access to one or more devices responsible for the prospective occurrence of the distractive event. For example, the access may be controlled by hiding information on a one or more devices that may otherwise distract the user (such as hiding weather, traffic, news, messages, buttons, or any other information likely to distract the user on devices such as a smart mirror, a mobile device, or any other device). The access may be controlled in this way when the user engages in the personal care activity and until the user finishes performing the personal care activity. The access may also be controlled, for example, by hiding (or at least partly hiding) app icons on a smartphone, tablet television or other device. For example, this may occur at the same time as displaying a message relating to the personal care activity (for example, a messaging such as 'tooth brushing') on part of the screen (such as in the middle of the screen) of the device to discourage engagement in secondary activities while performing the personal care activity.

In another example, the initiation of one or more countermeasures may comprise controlling one or more devices to place a preventative measure on a source of the prospective occurrence of the distractive event. For example, a notification (such as a message notification, a phone call notification, an app notification, or any other notification) may be temporarily blocked or postponed on one or more devices (such as a mobile device, e.g. a phone, tablet, television, or similar, a wearable device, a smart mirror, or any other device). The notification may be temporarily blocked or postponed until it is detected that the user has finished the personal care activity or until after a pre-defined time period for the personal care activity has expired. In some examples, a notification may be initiated when the user engages in a secondary activity (i.e. an activity aside from the personal care activity) to persuade the user to stop the secondary activity. For example, when performing a tooth care activity, the notification may read "Did you know that you brush your teeth much more effectively if you do not watch X at the same time?", or similar. In some embodiments, the system may be capable for use as a coaching system. For example, the user may be rewarded by the system when they avoid or stop a secondary activity.

As described with reference to the embodiment illustrated in FIG. 3, the user can be monitored and when indications of a distraction are detected, a notification can be provided to warn the user of the distraction.

Figure 4:
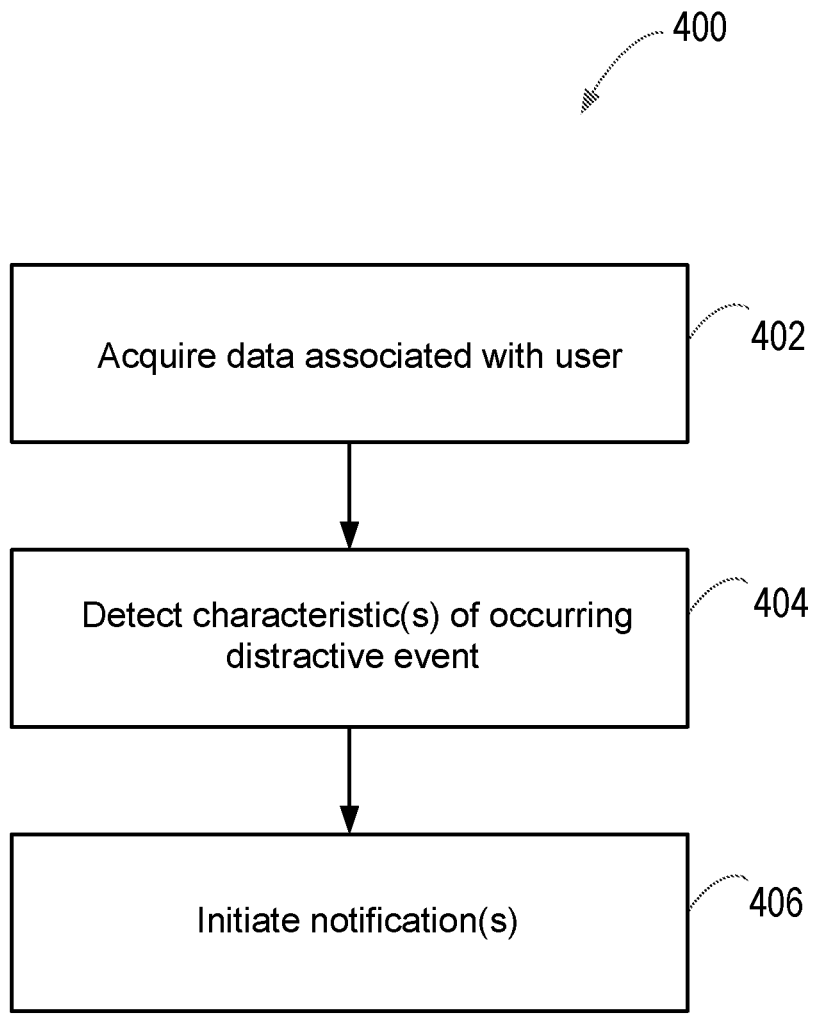
FIG. 4 is a flow chart illustrating a method for use in assisting a user to focus on performing a personal care activity according to another example embodiment.

FIG. 4 illustrates a method 400 for use in assisting a user to focus on performing a personal care activity according to another example embodiment. The illustrated method 400 can generally be performed by or under the control of the processing unit 102 of the system 100. In this example embodiment, it is possible to identify situations where a loss of focus by the user may occur, or has occurred, to then provide a notification to allow the user to focus, or re-focus their attention to the personal care activity.

With reference to FIG. 4, at block 402, data associated with the user is acquired during the personal care activity. In other words, the method described above with respect to block 202 of FIG. 2 is performed and thus the corresponding description will be understood to apply but will not be repeated here. In this embodiment, the data associated with the user during the personal care activity may be acquired from one or more sensors 106, which can comprise sensors in the personal care device used in the personal care activity, sensors in other devices, and/or sensors in the environment of the user. The data acquired may be provided directly to the processing unit 102 from the one or more sensors 106 or may be pre-processed by the one or more sensors 106 to identify relevant sections of data that are then provided to the processing unit 102, as described in more detail earlier.

At block 404, the acquired data is processed to detect at least one characteristic indicative of a distractive event occurring for the user in performing the personal care activity. For example, the acquired data is monitored and may be compared to characteristics indicative of distractive events (i.e. pre-defined signatures of distractive events) stored in a memory unit (such as the memory unit 110 of the system 100 or an external memory unit) to detect at least one characteristic indicative of a distractive event occurring for the user in performing the personal care activity. The processing of the acquired data may be performed in the same manner described for block 204 of FIG. 2 and thus will not be repeated here but will be understood to apply. For example, the characteristics indicative of distractive events may be stored in the memory unit in the form of a look-up table (LUT).

The detection of at least one characteristic indicative of a distractive event occurring for the user may comprise one or more of detection of at least one characteristic indicating that a distractive event is occurring and at least one characteristic indicative of the distractive event causing a negative influence on the personal care activity. Examples of a negative influence on the personal care activity may comprise one or more of a loss of focus of the user in performing the personal care activity, a reduced quality of the personal care activity, and any other negative influence on the personal care activity. A negative influence on the personal care activity may be detected in any suitable way. In one example, detecting a negative influence on the personal care activity may comprise detecting that a continuity of a movement (such as a slow movement) of a personal care device used in the personal care activity is disrupted. This may be sensed via one or more accelerometers and/or one or more cameras. In another example, detecting a negative influence on the personal care activity may comprise detecting that a personal care device used in the personal care activity is taken away from a treatment surface (for example, the teeth in a tooth care activity, the skin in a skin care activity, the hair in a hair care activity, or similar). This may be sensed via one or more surface contact sensors and/or one or more pressure sensors.

In some embodiments, the comparison of the acquired data to the stored characteristics indicative of distractive events may involve logical processing to determine whether certain conditions (for example, at least two conditions) are true to detect at least one characteristic indicative of a distractive event occurring. In an example involving two conditions, a first condition may be that a potentially distractive event is occurring (such as information being displayed on a screen of a device) and a second condition may be that the user is actually distracted by the distractive event (such as the user facing the screen of the device). In this example, if both the first and second condition are determined to be true, at least one characteristic indicative of a distractive event occurring is detected.

When at least one characteristic indicative of a distractive event occurring is detected, one or more actions associated with the detected at least one characteristic can be retrieved from the memory unit (such as from a lookup table). As mentioned earlier, in some cases, a characteristic may be stored with a plurality of associated actions. In other words, various actions may be possible for a single characteristic. In these cases, one or more of the actions associated with the characteristic may be selected based on one or more predefined selection criteria (as described earlier with reference to FIG. 2).

At block 406, one or more notifications associated with the detected at least one characteristic indicative of the distractive event are initiated to prompt the user to focus on the personal care activity. For example, this may comprise rendering a visual notification to the user, an audio notification to the user, a haptic notification to the user, a functional notification to one or more devices used in the personal care activity, or any other notification, or any combination of notifications. As mentioned earlier, the notification may act as a warning to the user of a distractive event to encourage the user to remain focussed on the personal care activity. The notification is designed to be noticed by the user and can convey a message to the user that will encourage them to focus on the personal care activity (for example, a message to ignore a distractive event).

In some embodiments, the one or more notifications associated with the detected at least one characteristic indicative of the distractive event may be initiated when at least one characteristic indicating that a distractive event is occurring is detected. In other embodiments, the one or more notifications associated with the detected at least one characteristic indicative of the distractive event may be initiated only when both of at least one characteristic indicating that a distractive event is occurring and at least one characteristic indicative of the distractive event causing a negative influence on the personal care activity are detected.

It will be understood that, in some embodiments, both the method described with reference to FIG. 3 and the method described with reference to FIG. 4 can be performed. For example, the at least one characteristic indicative of the distractive event may comprise at least one characteristic indicative of a prospective occurrence of a distractive event for the user in performing the personal care activity and at least one characteristic indicative of a distractive event occurring for the user in performing the personal care activity. Thus, both notifications and counter-measures may be initiated.

In any of the embodiments described herein, prior to processing the acquired data to detect at least one characteristic indicative of a distractive event (i.e. prior to block 204 of FIG. 2, block 304 of FIG. 3, or block 404 of FIG. 4), the method may further comprise identifying the user with which the acquired data is associated. In this way, it is possible to check that the acquired data is associated with the user that is performing the personal care activity. For example, identifying the user with which the acquired data is associated may comprise checking if the user performing the personal care activity has left or entered a room (such as by using facial recognition with a camera, a body weight sensing device in a floor mat, a weighing scale in front of a bathroom sink, or similar), checking if the personal care device used in performing the personal care activity has left or entered a room (such as by sensing a proximity of the device through its wireless signals, electromotive force EMF, sound, or any other property associated with the personal care device), checking the identity of the user switching on/off or picking up/putting down the personal care device (such as by use of fingerprint sensors), monitoring where users are in an environment (such as where multiple family members are in a home network), or any other way of identifying the user with which the acquired data is associated to check that the data is associated with the user that is performing the personal care activity. In this way, the system can be used in a multi-user environment.

In one multi-user embodiment, one or more actions may be initiated if the same user performing the personal care activity is identified to also be the user performing a secondary activity. For example, one or more actions may be initiated if the same user using a personal care device is identified to also be the user using another device. On the other hand, the one or more actions may not be initiated in a situation where a user using a personal care device is identified to be different to a user using another device. This may be the case where the user of the personal care device is in a different room to the user of the other device.

In any of the embodiments described herein (for example, with reference to FIG. 2, FIG. 3, or FIG. 4), the method may further comprise detecting whether the one or more initiated actions (such as the one or more initiated notifications or the one or more initiated counter-measures) are successful in assisting the user to focus on the personal care activity. For example, this may be detected by measuring a quality of the personal care activity such as by measuring the contact of the personal care device with a treatment area (such as the teeth, skin, hair, or any other treatment area, via e.g. one or more contact sensors, pressure sensors, and/or cameras), correct movement and/or orientation of the personal care device over the treatment area (e.g. smooth continuous movement, via e.g. an accelerometer, gyroscope, or any other movement or orientation sensor). In these embodiments, if one or more initiated actions are not successful in assisting the user to focus on the personal care activity, one or more further actions may be initiated to assist the user in focussing on the personal care activity. The further actions can be a repetition of one or more previous actions (for example, repeating one or more notifications or repeating one or more counter-measures), or can be an initiation of another action, which may be initiated using another communication channel (for example, sound instead of visual) or using another method (for example, turning off the distracting activity).

In any of the embodiments described herein, the method or methods may be repeated (for example, performed in a loop). In this case, data can be collected to gauge the effect of initiated actions on the focus of the user. In this way, the system can be refined to use the most successful actions in the future.

Therefore, as described above, there is provided an improved system and method for use in assisting a user to focus on performing the personal care activity. Specifically, the system and method assists the user to focus on performing a personal care activity through the initiated actions associated with any distractive events. For example, the system and method can reduce the likelihood of the user being distracted whilst performing a personal care activity through the use of counter-measures and, if the user is distracted, the user can be provided with a notification that will allow them to modify their behaviour and re-focus. In this way, the user achieves improved results from the personal care activity. The system and method can be employed in many settings, including at a home of the user or at any other location the user may perform a personal care activity.

There is also provided a computer program product comprising a computer readable medium, the computer readable medium having computer readable code embodied therein, the computer readable code being configured such that, on execution by a suitable computer or processor, the computer or processor is caused to perform the method or methods described herein.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for use in assisting a user to focus on performing a personal care activity using a personal care device, the system comprising:
    at least one sensor configured to acquire data associated with the user;
    a memory unit for storing characteristics indicative of distractive events and associated actions to assist the user in focussing on the personal care activity; and
    a processing unit configured to:
        receive the data from the at least one sensor, wherein the data indicates movement of the user during the personal care activity;
        compare the received data to the stored characteristics indicative of distractive events to detect at least one characteristic indicative of a distractive event for the user in performing the personal care activity when the movement of the user indicates performance of the distractive event, increasing a risk of the user losing focus on the personal care activity being performed, which would result in negatively impacting quality and/or effectiveness of the personal care activity being performed; and
        initiate one or more actions associated with the detected at least one characteristic indicative of the distractive event to assist the user in focussing on the personal care activity,
    wherein the at least one characteristic indicative of the distractive event comprises a pattern of unusual head motions not associated with a focused performance of the personal care activity.

2. The system as claimed in claim 1, wherein:
    the detected at least one characteristic indicative of the distractive event is associated with a plurality of actions to assist the user in focussing on the personal care activity; and
    the processing unit is configured to select the one or more actions associated with the detected at least one characteristic indicative of the distractive event to be initiated to assist the user in focussing on the personal care activity.

3. The system as claimed in claim 2, wherein the one or more actions are selected based on one or more of: a ranking assigned to the plurality of actions, an availability of the plurality of actions at a time for initiating the one or more actions, or a condition of the user.

4. The system as claimed in claim 1, wherein the at least one sensor is configured to pre-process the acquired data to identify sections of data that are relevant.

5. The system as claimed in claim 1, wherein the at least one sensor comprises one or more of:
    a visual sensor;
    a motion sensor;
    a presence sensor; and
    a proximity sensor.

6. The system as claimed in claim 1, wherein the at least one characteristic indicative of the distractive event comprises a characteristic indicative of a prospective occurrence of the distractive event for the user in performing the personal care activity.

7. The system as claimed in claim 1, wherein the one or more actions comprise one or more counter-measures associated with the detected at least one characteristic indicative of the distractive event to reduce a likelihood of the distractive event distracting the user.

8. The system as claimed in claim 7, wherein the processing unit is configured to initiate the one or more counter-measures by one or more of:
    rendering a visual, audio, haptic and/or functional stimulus to the personal care device;
    controlling access to one or more devices responsible for prospective occurrence of the distractive event; and
    placing a preventative measure on a source of the prospective occurrence of the distractive event.

9. The system as claimed in claim 1, wherein the processing unit is configured to initiate one or more notifications associated with the detected at least one characteristic indicative of the distractive event to prompt the user to focus on the personal care activity.

10. The system as claimed in claim 9, wherein the processing unit is configured to initiate one or more notifications by rendering one or more of:
    a visual notification to the user;
    an audio notification to the user;
    a haptic notification to the user; and
    a functional notification to the personal care device.

11. The system as claimed in claim 1, wherein the at least one characteristic indicative of the distractive event comprises a pattern of motion of the personal care device not associated with a focused performance of the personal care activity.

12. A method performed by a processing unit for use in assisting a user to focus on performing a personal care activity performed using a personal care device, the method comprising:
    acquiring data associated with the user while performing the personal care activity, wherein the data indicates movement of the user during the personal care activity;
    comparing the acquired data to characteristics indicative of distractive events stored in a memory that stores the characteristics indicative of distractive events and associated actions to assist the user in focussing on the personal care activity;
    identifying at least one characteristic indicative of a distractive event for the user in performing the personal care activity when the movement of the user indicates performance of the distractive event, increasing a risk of the user losing focus on the personal care activity being performed, which would result in negatively impacting quality and/or effectiveness of the personal care activity being performed;

identifying at least one associated action previously associated with the identified at least one characteristic; and initiating the at least one associated action to assist the user in focussing on the personal care activity, wherein the at least one characteristic indicative of the distractive event comprises a pattern of unusual head motions not associated with a focused performance of the personal care activity.

13. The method of claim 12, wherein the at least one characteristic indicative of the distractive event comprises a characteristic indicative of a prospective occurrence of the distractive event for the user in performing the personal care activity.

14. The method of claim 13, wherein the at least one associated action comprises one or more counter-measures associated with the at least one characteristic indicative of the prospective occurrence of the distractive event to reduce a likelihood of the distractive event distracting the user, and wherein initiating the one or more counter-measures comprises rendering a visual, audio, haptic and/or functional stimulus to the personal care device.

15. The method of claim 12, wherein initiating the at least one associated action to assist the user in focussing on the personal care activity comprises initiating one or more notifications associated with the at least one characteristic indicative of the distractive event to prompt the user to focus on the personal care activity.

16. The method of claim 15, wherein initiating the one or more notifications comprises rendering one or more of:
a visual notification to the user;
an audio notification to the user;
a haptic notification to the user; and
a functional notification to the personal care device.

17. The method as claimed in claim 12, further comprising:
acquiring data from at least one sensor indicating a start of the personal care activity.

18. A system for use in assisting a user to focus on performing a personal care activity using a personal care device the system comprising:
at least one sensor configured to acquire data associated with the user;
a memory unit for storing characteristics indicative of distractive events and associated actions to assist the user in focussing on the personal care activity; and
a processing unit configured to:
receive the data from the at least one sensor, wherein the data indicates movement of the user during the personal care activity;
compare the received data to the stored characteristics indicative of distractive events to detect at least one characteristic indicative of a distractive event for the user in performing the personal care activity when the movement of the user indicates performance of the distractive event, increasing a risk of the user losing focus on the personal care activity being performed, which would result in negatively impacting quality and/or effectiveness of the personal care activity being performed; and
initiate one or more actions associated with the detected at least one characteristic indicative of the distractive event to assist the user in focussing on the personal care activity,
wherein the processing unit is further configured to compare the received data to the stored characteristics indicative of distractive events to detect actions of the user indicative of the user performing a secondary activity that is not related to the personal care activity.

\* \* \* \* \*